Figure 1:
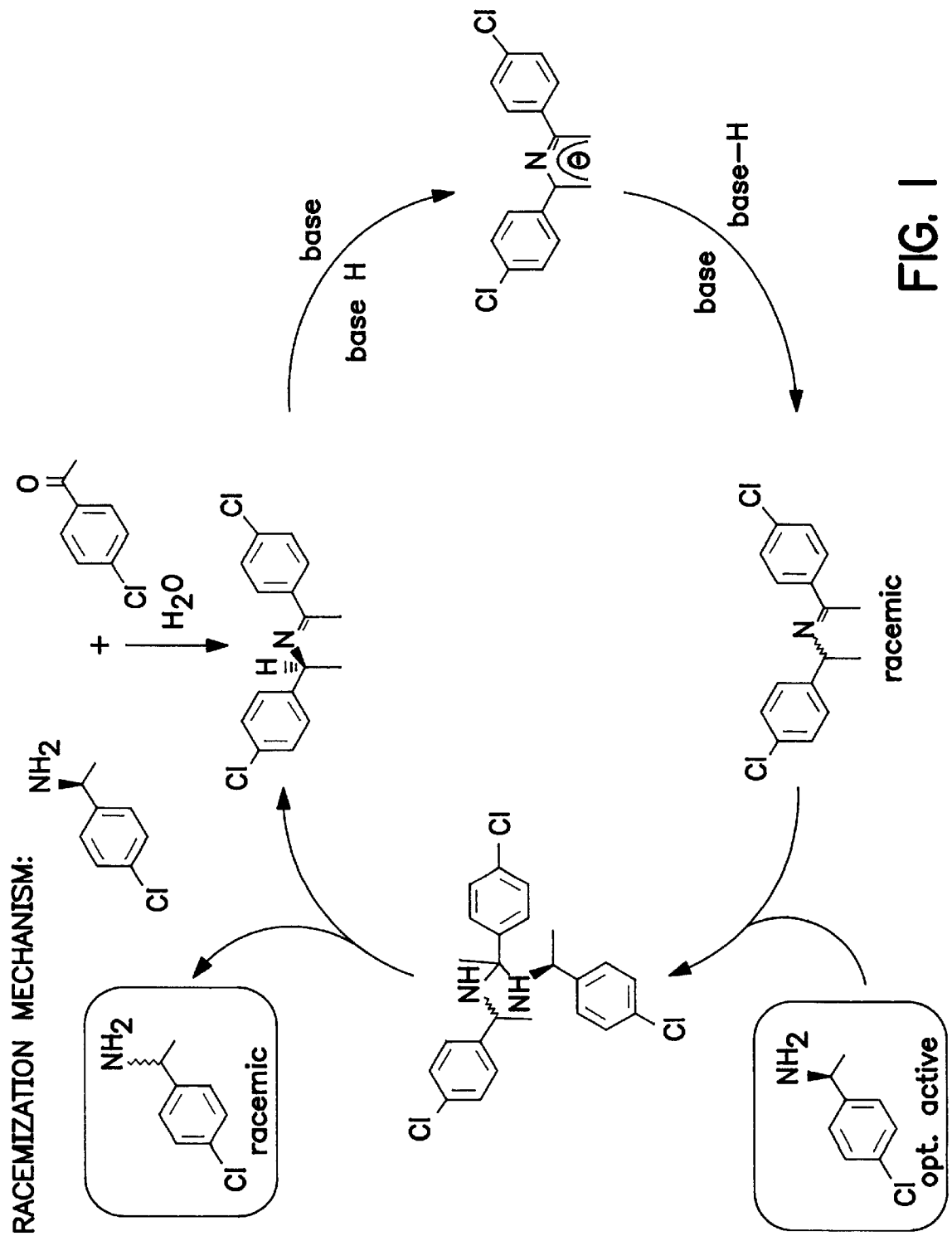

United States Patent

Ditrich

Patent Number: 5,847,215
Date of Patent: Dec. 8, 1998

[54] RACEMIZATION OF OPTICALLY ACTIVE AMINES

[75] Inventor: Klaus Ditrich, Gönnheim, Germany

[73] Assignee: BASF Aktiengesellschaft, Ludwigshafen, Germany

[21] Appl. No.: 798,336

[22] Filed: Feb. 10, 1997

[30] Foreign Application Priority Data

Feb. 20, 1996 [DE] Germany ............ 196 06 124.5

[51] Int. Cl.⁶ .................. C07C 209/82; C07C 209/88; C07C 209/86
[52] U.S. Cl. ............... 564/302; 564/272; 564/275; 564/384; 564/388
[58] Field of Search ............... 564/302, 272, 564/275, 384, 388

[56] References Cited

U.S. PATENT DOCUMENTS

| 5,183,939 | 2/1993 | Jansen et al. ............ 564/302 |
| 5,679,857 | 10/1997 | Hijiya et al. ............ 564/304 |

FOREIGN PATENT DOCUMENTS

| 489682 | 6/1992 | European Pat. Off. . |
| 2851039 | 6/1980 | Germany . |
| 07188120 | 12/1993 | Japan . |

*Primary Examiner*—Richard L. Raymond
*Attorney, Agent, or Firm*—Keil & Weinkauf

[57] ABSTRACT

A process for the racemization of optically active amines of the formula (I), where Ar is an unsubstituted or substituted aryl and R is alkyl, in which a) (I) is reacted with the ketone (II) in which Ar and R have the same meanings as for (I), to give the condensation product (III),

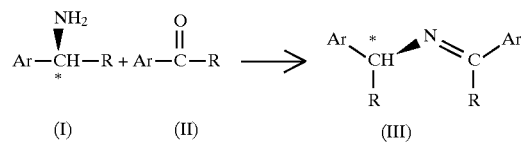

b) (III) is racemized by treatment with base,

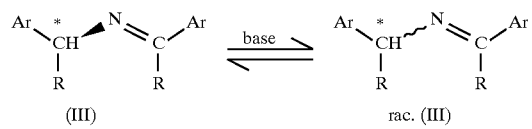

c) the arylalkylamine (I) is liberated as racemate from racemic (III) by reaction with optically active (I).

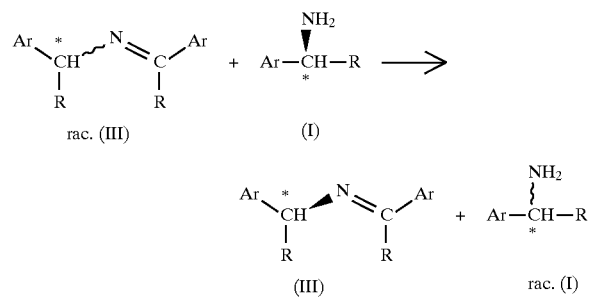

4 Claims, 1 Drawing Sheet

RACEMIZATION OF OPTICALLY ACTIVE AMINES

The present invention relates to a process for the racemization of optically active amines.

Optically active amines are employed as intermediates in a number of syntheses of active substances. In these as a rule only one optical antipode is required, whereas the other antipode results as byproduct. In order to make these synthetic processes more economic, it is worthwhile to racemize the unwanted antipode and prepare the required antipode anew from this racemic mixture.

DE 28 51 039 discloses a process for the racemization of 1-arylalkylamines by reaction with hydrogen/Raney cobalt. However, under these conditions, unwanted side reactions such as dehalogenation on the aryl radical also take place, so that this process is unsuitable for many arylalkylamines.

EP 489 682 describes a process for the racemization of optically active 1-arylalkylamines in which the amines are reacted with metal alkanolates in dimethyl sulfoxide. However, this process is not very suitable for use on the industrial scale because it requires costly reagents, needs an additional neutralization step and does not allow a continuous procedure.

JP 07188120 describes the racemization of optically active 1-(halophenyl)ethylamines which comprises the following process steps:

(i) condensation of the 1-(halophenyl)ethylamine with an acetophenone,
(ii) heating of the condensation product in the presence of alkali metal alkoxide and
(iii) hydrolysis.

This process is likewise a batchwise process in which a number of additional workup steps (acidification, extraction of the acetophenone, liberation of the amine with base) are necessary.

It is an object of the present invention to provide a process for the racemization of optically active arylalkylamines which does not have the disadvantages of the abovementioned processes.

We have found that this object is achieved by a process for the racemization of optically active amines of the formula (I), where Ar is an unsubstituted or substituted aryl and R is alkyl, in which a) (I) is reacted with the ketone (II) in which Ar and R have the same meanings as for (I), to give the condensation product (III)

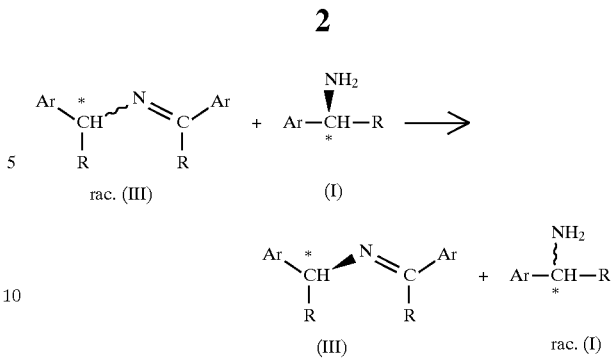

b) (III) is racemized by treatment with base,

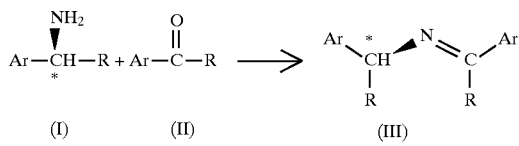

c) the arylalkylamine (I) is liberated as racemate from racemic (III) by reaction with optically active (I).

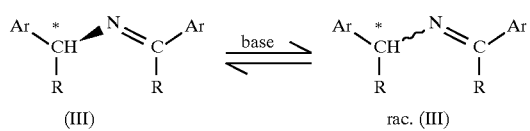

Optically active amines (I) which can be employed for the process according to the invention are the pure R or S forms of (I) or else mixtures of R and S forms of (I) in any ratios of amounts.

Ar in the general formula for (I) is an aryl, preferably phenyl or naphthyl, which is unsubstituted or substituted once to five times, identically or differently. The possible substituents are preferably selected from the group consisting of halogen, nitro, cyano, open-chain or cyclic alkyl, alkoxy and alkylthio. Said alkyl, alkoxy and alkylthio substituents can themselves in turn be substituted by, for example, one or more halogen atoms.

Particularly preferred compounds (I) are those in which Ar is phenyl substituted by electron-attracting radicals. Singly substituted halophenyls, for example 2-, 3- or 4-chlorophenyl, are very particularly preferred.

R in the general formula for (I) is an unsubstituted or substituted straight-chain or branched alkyl, preferably with 1 to 10, in particular with 1 to 5, carbon atoms. R is very particularly preferably methyl.

The compounds (II) are aryl ketones in which the meanings of Ar and R are the same as for the compounds (I). It is a particular characteristic of the process according to the invention that the ketones (II) employed are identical to the amines (I) in respect of the radicals Ar and R.

The ketones (II) are reacted with the amines (I) in a condensation reaction (a). This reaction can be carried out with conventional solvents or else without solvent. The process according to the invention is preferably carried out without solvent. The reaction is normally carried out at from 0° to 300°, preferably from 20° to 200° C. The condensation product (III) resulting from this is a Schiff's base which is racemized by addition of a base (b).

Suitable bases are alcoholates such as sodium or potassium methanolate, sodium or potassium ethanolate, sodium or potassium t-butanolate or tertiary amines, especially diazabicyclooctane (Dabco), diazabicyclononene (DBN), diazabicycloundecene (DBU) and tri-n-octylamine.

The amine (I) is liberated in racemic form from the condensation product (III) by reaction with optically active (I) (c).

The amount of ketone (II) added can vary within wide limits because (II) is recovered in the process. If rapid racemization is required, it is appropriate to increase the amount of (II); on the other hand, smaller amounts of (II) may suffice if the racemization time is extended to compensate. (II) is preferably employed in an amount of from 1 to 10 mol % based on (I).

The process according to the invention is, as a rule, carried out under atmospheric pressure. However, it can also be carried out under reduced or elevated pressure.

After the racemization reaction has taken place, the racemic amine (I) is isolated by conventional methods, for example by distillation, from the reaction mixture.

It is not necessary in this case to discard the distillation residue; on the contrary it can be used for further racemization by reacting this residue with further optically active I and carrying out the racemization reaction again.

This process is therefore particularly suitable for continuous operation by the procedure depicted in FIG. 1.

EXAMPLE

Racemization of S-1-(4-chlorophenyl)ethylamine 10.0 g of S-1-(4-chlorophenyl)ethylamine (ee=100%) were mixed with 1.0 g of 4-chloroacetophenone and heated at 100° C. for two hours, and then 1.0 g of diazabicycloundene (DBU) was added. The temperature was raised to 190° C. After 80 hours, the amine had completely racemized. Distillation resulted in 8.0 g of racemic 1-(4-chlorophenyl) ethylamine.

The distillation residue was mixed with optically active 1-(4-chlorophenyl)ethylamine and employed again for the racemization.

I claim:

1. A process for the racemization of optically active amines of the formula (I), where Ar is an unsubstituted or substituted aryl and R is alkyl, in which a) (I) is reacted with the ketone (II) in which Ar and R have the same meanings as for (I), to give the condensation product (III),

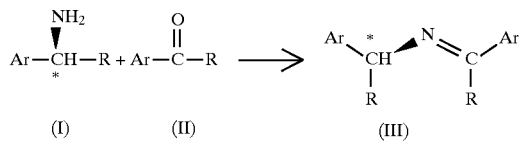

b) (III) is racemized by treatment with base,

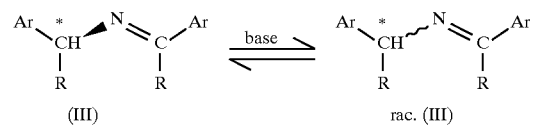

c) the arylalkylamine (I) is liberated as racemate from racemic (III) by reaction with optically active (I),

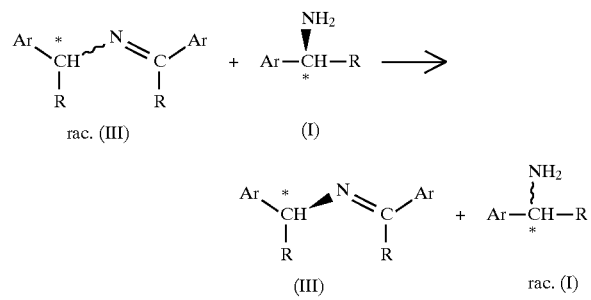

2. A process as claimed in claim 1, wherein Ar in formula (I) is phenyl or naphthyl which is unsubstituted or substituted once to five times, identically or differently, by halogen, nitro, cyano, open-chain or cyclic alkyl, alkoxy or alkylthio, and R is an unsubstituted or substituted straight-chain or branched alkyl with 1 to 10 carbon atoms.

3. A process as claimed in claim 2, wherein Ar is chlorophenyl and R is methyl.

4. A process as claimed in claim 1, which is carried out continuously.

* * * * *